(12) United States Patent
Ahn et al.

(10) Patent No.: US 8,916,685 B2
(45) Date of Patent: Dec. 23, 2014

(54) FUSION PROTEIN COMPRISING SMALL HEAT SHOCK PROTEIN, CAGE PROTEIN FORMED THEREBY, AND NOVEL USE THEREOF

(75) Inventors: Hyung-Jun Ahn, Seoul (KR); Ick-Chan Kwon, Seoul (KR); Kul-Won Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 6 days.

(21) Appl. No.: 13/702,752

(22) PCT Filed: Jun. 7, 2011

(86) PCT No.: PCT/KR2011/004150
§ 371 (c)(1),
(2), (4) Date: Dec. 7, 2012

(87) PCT Pub. No.: WO2011/162492
PCT Pub. Date: Dec. 29, 2011

(65) Prior Publication Data
US 2013/0230562 A1    Sep. 5, 2013

(30) Foreign Application Priority Data
Jun. 23, 2010 (KR) ................. 10-2010-0059567

(51) Int. Cl.
| | |
|---|---|
| C07K 14/00 | (2006.01) |
| A61K 47/42 | (2006.01) |
| C07K 14/47 | (2006.01) |
| C12Q 1/37 | (2006.01) |
| G01N 33/542 | (2006.01) |
| C07K 14/435 | (2006.01) |

(52) U.S. Cl.
CPC ............. *A61K 47/42* (2013.01); *C07K 14/47* (2013.01); *C12Q 1/37* (2013.01); *G01N 33/542* (2013.01); *C07K 14/435* (2013.01); *C07K 2319/21* (2013.01); *G01N 2333/96466* (2013.01); *G01N 2333/96494* (2013.01); *G01N 2510/00* (2013.01)
USPC ........................................... 530/350

(58) Field of Classification Search
CPC .. C07K 14/00; C07K 14/195; C07K 2319/00; C07K 2319/21; C07K 2319/50; C07K 2319/735; C12Q 1/37
USPC ............. 530/350; 435/7.4, 7.72, 23, 24
See application file for complete search history.

(56) References Cited

U.S. PATENT DOCUMENTS

2004/0002128 A1* 1/2004 Chang et al. ............ 435/23
2006/0099689 A1* 5/2006 Mertens et al. .......... 435/69.7

FOREIGN PATENT DOCUMENTS

| WO | WO 2008/127019 A1 * | 10/2008 |
|---|---|---|
| WO | WO 2010019725 A2 * | 2/2010 |
| WO | WO 2010/024609 A2 * | 3/2010 |

OTHER PUBLICATIONS

Pham et al., Bioconjugate Chem. 15:1403-1407, 2004.*
Flenniken et al., Chem. Biol. 13:161-170, 2006.*
Ford et al., Prot. Exp. Purif. 2:95-107, 1991.*
Pham et al., Bioconjugate Chem. 14:1048-1051, 2003.*
International Search Report of Corresponding PCT Application PCT/KR2011/004150 mailed Feb. 6, 2012.
William H. Eschenfeldt et al., "Cleavable C-terminal His-tag vectors for structure determination", *J Struct Funct Genomics*, Mar. 2010, pp. 1-15.
Pall Corporation, "Purification of Polyhistidine-Tagged Recombinant Proteins With IMAC Hyper-Cel™ Resin Using AcroPrep ™ 96-well Filter Plates or Nanosep® Centrifugal Devices", 2008, pp. 1-6.
Rosalind Kim et al., "Small heat shock protein of *Methanococcus jannaschii*, a hyperthermophile", Proc. Natl. Acad. Sci. USA, vol. 95, Aug. 1998, pp. 9129-9133.
Coleen R. Kaiser et al., "Biodistribution studies of protein cage nanoparticles demonstrate broad tissue distribution and rapid clearance in vivo", International Journal of Nanomedicine 2007, pp. 715-733.
Michelle L. Flenniken et al., "The Small Heat Shock Protein Cage from *Methanococcus jannaschii* Is a Versatile Nanoscale Platform for Genetic and Chemical Modification", Nano Letters, 2003, vol. 3, No. 11, pp. 1573-1576.
Qiagen, "The QIAexpressionist™", A handbook for high-level expression and purification of 6xHis-tagged proteins, Fifth Edition, Jun. 2003, pp. 1-126.
Niraj H. Tolia et al., "Strategies for protein coexpression in *Escherichia coli*", Nature Methods, vol. 3, No. 1, pp. 55-64, Jan. 2006.
Barbara Lelj-Garolla et al., "Self-association of a Small Heat Shock Protein", J Mol Biol., Jan. 21, 2005, pp. 631-642.

* cited by examiner

*Primary Examiner* — David J Steadman
(74) *Attorney, Agent, or Firm* — Staas & Halsey LLP (57) ABSTRACT

The present invention relates to a fusion protein comprising small heat shock protein, a cage protein formed thereby, and novel use thereof, more particularly, a fusion protein comprising a small heat shock protein, a recognition site of a protease, and a histidine polymer, wherein the recognition site and the histidine polymer are sequentially linked to a carboxyl terminal of the small heat shock protein, a cage protein formed thereby, and novel use thereof. The fusion protein of the present invention, and a cage protein formed by the self-assembly properties of the fusion protein are not cytotoxic, and emits a fluorescence signal of about 20 to about 50 times higher comparing to a single peptide for the conventional molecular imaging, per unit protein. Additionally, cell permeability is very excellent, thereby to be effectively used as a biosensor or a bioactive material carrier.

9 Claims, 7 Drawing Sheets
(3 of 7 Drawing Sheet(s) Filed in Color)

```
                    10         20         30         40         50         60
                    |          |          |          |          |          |
ApoHsp      MFGRDPFDSLFERMFKEFFATPMTGTTMIQSSTGIQISGKGFMPISIIEGDQHIKVIAWL
Hsp         MFGRDPFDSLFERMFKEFFATPMTGTTMIQSSTGIQISGKGFMPISIIEGDQHIKVIAWL
            ************************************************************

Prim.cons.  MFGRDPFDSLFERMFKEFFATPMTGTTMIQSSTGIQISGKGFMPISIIEGDQHIKVIAWL

70         80         90        100        110        120
                    |          |          |          |          |          |
ApoHsp      PGVNKEDIILNAVGDTLEIRAKRSPLMITESERIIYSEIPEEEEIYRTIKLPATVKEENA
Hsp         PGVNKEDIILNAVGDTLEIRAKRSPLMITESERIIYSEIPEEEEIYRTIKLPATVKEENA
            ************************************************************

Prim.cons.  PGVNKEDIILNAVGDTLEIRAKRSPLMITESERIIYSEIPEEEEIYRTIKLPATVKEENA 130        140        150        160
                    |          |          |          |
ApoHsp      SAKFENGVLSVILPKAESSIKKGINIEGGDEVDGGCHHHHHH    SEQ ID NO: 5
Hsp         SAKFENGVLSVILPKAESSIKKGINIE---------------    SEQ ID NO: 6
            ***************************

Prim.cons.  SAKFENGVLSVILPKAESSIKKGINIEGGDEVDGGCHHHHHH    SEQ ID NO: 5
```

FUSION PROTEIN COMPRISING SMALL HEAT SHOCK PROTEIN, CAGE PROTEIN FORMED THEREBY, AND NOVEL USE THEREOF

CROSS-REFERENCE TO RELATED APPLICATIONS

This application is a U.S. national stage application of PCT/KR2011/004150 filed Jun. 7, 2011 and claims the priority benefit of Korean Application 10-2010-0059567 filed Jun. 23, 2010 in the Korean Intellectual Property Office, the contents of both of which are incorporated herein by reference.

FIELD OF THE INVENTION

The present invention relates to a fusion protein comprising small heat shock protein, a cage protein formed thereby, and novel use thereof, more particularly, a fusion protein comprising a small heat shock protein, a recognition site of a protease, and a histidine polymer, wherein the recognition site and the histidine polymer are sequentially linked to a carboxyl terminal of the small heat shock protein, a cage protein formed thereby, and novel use thereof.

BACKGROUND OF THE INVENTION

A cage protein is a protein to form a macromolecule having a molecular weight of dozens to hundreds times of a monomer by self-assembly properties of a low molecular weight monomer. Virus capsid protein, ferritin, heat shock protein, Dps protein belong to the cage protein in nature. Each monomer to form the cage protein has a very regular and precise interaction with adjacent monomer and inside of the cage is empty. Since the inside of the cage is isolated from the outside by the nature such as the container of the cage protein, the cage protein is frequently used as a drug delivery system in the field of medicine.

Specially, a small heat shock protein, HSP is classified into five families of HSP100, HSP90, HSP70, HSP60 and smHSP according to a molecular weight. These are known to be induced by stress stimuli including nutritional deficiencies, metabolic disorders, oxygen radicals and cellular pathogen infection (Welch May, 1993, Scientific American 56-64; Young, 1990, Annu. Rev. Immunol. 8: 401-420; Craig, 1993, SCIENCE 260: 1902-1903; Gething et al., 1992, Nature 355: 33-45; and Lindquist et al., 1988, Annu. Rev. Genetics 22: 631-677).

Meanwhile, proteases regulate diverse cellular functions in a wide range and these functions are done through the degradation of bioactive material. Thus, function and role of the proteases are very important to vital phenomenon of all living things. For example, deficiency, lack or over-expression of a specific protease lead to a significant result, that is cancer, arthritis, neurodegenerative diseases, cardiovascular, autoimmune inflammatory diseases, and so on may occur. Thus, proteases and substrates thereof are major targets for a new drug development and a matter of interest in the pharmaceutical industry.

Roles of proteases in vitro and in vivo are actively studied due to various roles of proteases and recently completed genome projects. According to the human genome projects, more than about 500 of human genes were found to be related to proteases. Recently, it has been newly disclosed that protease plays a pivot role and provides cause in human diseases such as cancer and Alzheimer's disease.

For example, metal matrix protease (MMP) has been recognized as a factor to degrade extracellular matrix in the cell and in vivo in the past, however, MMP were identified to be involved in integrin signaling and cell movement according to degradation of pericellular matrix through various studies. In addition, MMP has been disclosed to play an important role in the cancer growth such as angiogenesis, tumor cell invasion and metastasis.

Apoptosis has been also in the spotlight in the field of life science in the last decade and known to play an important role in embryonic development, immune response and tissue homeostasis (Vaux, D. L. et al. 1999). In case there occurs something wrong with apoptosis, incurable diseases such as cancer or neurodegenerative disorder may occur (Nicholson, D. W. 1996). A large number of enzymes are involved in apoptosis. Among them, apoptosis typically begins by caspase which is protease activated after activation of death receptor.

As described above, physiological functions of various proteases will be newly illuminated according to disclosure of new substrates, thereby target proteins for a new drug are expected to be developed.

However, there are no methods to detect by imaging activity of a specific protease, or non-invasive imaging techniques for detecting expression level of proteases in vivo, so development of related technology is urgently required. For representative methods of measurement of protease, there are 2-D gels and multi-performance liquid chromatography, Enzyme-Linked ImmunoSorbent Assay (ELISA) or a method to measure peak shift with spectroscopy by combining a fluorescent substrate with protease-specific peptide substrate.

However, these methods require multi-step protocol to measure, especially if a peptides itself is used, synthesis and purification processes are cumbersome and costs high. There are also disadvantages of cytotoxicity and significantly low cell permeability.

SUMMARY OF THE INVENTION

While studying about a biosensor for detecting protease, the present inventors prepared a fusion protein comprising a small heat shock protein and a cage protein formed by the fusion protein. The cage protein has no cytotoxicity and very high cell permeability and can be effectively used as a biosensor by increasing the signal intensity of a marker, thereby the present invention has been completed.

Accordingly, disclosed herein is a fusion protein comprising a small heat shock protein (Hsp), a recognition site of a protease, and a histidine polymer, wherein the recognition site and the histidine polymer are sequentially linked to a carboxyl terminal of the small heat shock protein.

In an embodiment, a cage protein formed by the fusion protein is also disclosed.

In an embodiment, a polynucleotide encoding the fusion protein is also disclosed.

In an embodiment, an expression vector comprising the polynucleotide is also disclosed.

In an embodiment, a transformant transformed with the expression vector is also disclosed.

In an embodiment, a biosensor for detecting a protease comprising the cage protein is also disclosed.

In an embodiment, a bioactive material carrier wherein the bioactive material is loaded inside the cage protein is also disclosed.

Solution to Problem

The present invention provides a fusion protein comprising a small heat shock protein (Hsp), a recognition site of a protease, and a histidine polymer, wherein the recognition site and the histidine polymer are sequentially linked to a carboxyl terminal of the small heat shock protein.

In addition, the present invention provides a cage protein formed by the fusion protein.

In addition, the present invention provides a polynucleotide encoding the fusion protein.

In addition, the present invention provides an expression vector comprising the polynucleotide.

In addition, the present invention provides a transformant transformed with the expression vector.

In addition, the present invention provides a biosensor for detecting a protease comprising the cage protein as an active ingredient.

In addition, the present invention provides a bioactive material carrier wherein the bioactive material is loaded inside the cage protein.

The terminology used in the present invention will be described in detail.

A small heat shock protein (Hsp) in the present invention may be used, without limitation, whatever if each of the small heat shock protein can form a complex protein in the form of cage as a unit. More preferably, the small heat shock protein may be selected from the group consisting of a polypeptide represented by the amino acid sequence of SEQ ID NO: 6 derived from *Methanococcus jannaschii*, a fragment and a variant thereof. The fragment and the variant may be not limited as long as the activity thereof to form the fusion protein in the form of cage is maintained, particularly, the variant may be prepared by addition, deletion or substitution of one or more amino acids in the amino acid sequence of SEQ ID NO: 6.

Instead of HSP, an active protein to form the fusion protein in the form of cage may be not limited to, preferably selected from the group consisting of ferritin protein derived from human (NCBI accession No: NP_002023.2, NP_000137.2), capsid protein derived from Hepatitis B virus (NCBI accession No: NP_647607.1), capsid protein derived from Tobacco mosaic virus (NCBI accession No: NP_597750.1) and capsid protein derived from Cowpea chlorotic mottle virus, CCMV (NCBI accession No: NP_613277.1).

A protease in the present invention may be not limited to, preferably selected from the group consisting of caspase, matrix metalloproteinases (MMP), cathepsin S and viral proteases, more preferably, may be caspase.

A recognition site of the protease in the present invention is a site which the protease recognizes to degrade a corresponding substrate and may be various according to a kind of the protease. Particularly, for caspase, the recognition site may be DEVD (Asp-Glu-Val-Asp) represented by SEQ ID NO: 8, for matrix metalloproteinases (MMP), the recognition site may be Ile-Pro-Val-Ser-Leu-Arg-Ser represented by SEQ ID NO: 10. In case cathepsin S, the recognition site may be Val-Val-Arg-Xaa represented by SEQ ID NO: 11, in case viral proteases, the recognition site may be Val-Ser-Gln-Asn-Tyr-Pro-Ile-Val-Gln-Asn represented by SEQ ID NO: 12.

When the recognition site does not comprise a cysteine residue, the cysteine residue may be preferably included in the carboxyl terminal or amino acid terminal of the recognition site additionally. That is intend to indicate the recognition site of the protease by inducing a covalent bond between a sulfhydryl group of the cysteine residue and a fluorescent dye, preferably, maleimide of fluorescent dye Cy5.5.

A length of the recognition site of the protease may be not limited to, consist of amino acid residues of 4 to 20.

A histidine polymer in the present invention may be not limited to, preferably a polymer which histidines of 6 to 20 are continuously polymerized, more preferably may be represented by SEQ ID NO: 9.

A cage protein in the present invention may be a complex protein comprising the fusion protein of the present invention as a unit. The cage protein may be a complex protein which the fusion proteins of the present invention are regularly arranged as a unit due to self-assembly properties of the small heat shock protein included in the fusion protein of the present invention.

A biosensor in the present invention may be a sensor to detect or measure a protease using a response mechanism of the protease.

Hereinafter, the present invention will be explained in detail.

A fusion protein of the present invention is characterized by comprising a small heat shock protein (Hsp), a recognition site of a protease, and a histidine polymer, wherein the recognition site and the histidine polymer are sequentially linked to a carboxyl terminal of the small heat shock protein.

The fusion protein of the present invention may play a role as a unit of a cage protein and may form a structure in the form of a cage by comprising the small heat shock protein (see Example 1-3). In addition, the fusion protein of the present invention may detect a specific protease by comprising the recognition site of a protease (see Experiment example 2 and Experiment example 4), and a cell permeability of the fusion protein may be remarkably high by comprising the histidine polymer (see Experiment example 1).

As described above, the recognition site in the fusion protein of the present invention is a site which the protease recognizes in order to degrade a corresponding substrate. When the protease is caspase, more preferably caspase-3 or caspase-7, most preferably caspase-3, the recognition site may be a DEVD motif comprising the amino acid sequence of SEQ ID NO: 8, more preferably may be represented by the amino acid sequence of SEQ ID NO: 7 comprising a cysteine residue.

The fusion protein of the present invention may be not limited to, preferably a fusion protein represented by the amino acid sequence of SEQ ID NO: 5, which a recognition site represented by the amino acid sequence of SEQ ID NO: 7 and a histidine polymer represented by the amino acid sequence of SEQ ID NO: 9 are sequentially linked to a carboxyl terminal of the small heat shock protein represented by the amino acid sequence of SEQ ID NO: 6.

The fusion protein of the present invention may be not limited to, preferably which a marker is inserted. The marker is a material to detect a specific amino acid sequence by forming covalent or non-covalent bond to a protein and may be not limited to, preferably an enzyme, a fluorescent substance, a radioactive isotope, a quencher or a chemical material.

The fluorescent substance may be a substance to emit fluorescence of red or near-infrared ray, but not limited to, preferably selected from the group consisting of cyanine, fluorescein, tetramethylrhodamine, Alexa, BODIPY and derivative thereof, more preferably may be a fluorescent dye Cy5.5. The fluorescent substance may be not limited to, marked to the recognition site.

The quencher may be a substance to quench fluorescence of the fluorescent substance, but not limited to, preferably selected from the group consisting of a blackhole quencher, a blackberry quencher and derivative thereof and a person skilled in the art can easily select according to the fluorescent substance. More preferably, when the Cy5.5 is used as the fluorescent substance, the blackhole quencher may be used as the quencher. The quencher may be not limited to, preferably labeled at the small heat shock protein. For example, when the blackhole quencher is used, the blackhole quencher may be labeled at a lysine residue of the small heat shock protein.

As described above, since the fluorescent substance is labeled at the recognition site and the quencher is labeled at the small heat shock protein, the fusion protein of the present invention may exhibit a quenching phenomenon without the protease, but fluorescence appears when the protease degradees the recognition site. Thus, the protease may be easily detected.

The fusion protein of the present invention may be not limited to, preferably inserted to a common vector made with a purpose for expression a foreign gene, so may be produced in large quantities with genetic engineering. The vector may be appropriately selected according to type or properties of host cells for the production of protein, or may be newly prepared. A method of transforming the vector to host cells and a method of producing recombinant proteins from a transformant may be easily carried out in usual manner. Methods for selection, production, transformation of the vector and expression of recombinant proteins may be easily carried out by one of ordinary skill in the art to which this invention belongs. Additionally, all such modifications are intended to be included within the scope of the present invention (see Example 1).

Meanwhile, the cage protein of the present invention may consist of the fusion protein of the present invention.

The cage protein of the present invention may be not limited to, preferably which the fusion proteins of the present invention of 24 are regularly arranged as unit. A mean molecular weight may be not limited to, preferably about 400 kDa to about 500 kDa.

The cage protein of the present invention may detect a specific protease by comprising the recognition site in the fusion protein of the present invention (see Experiment example 2 and Experiment example 4), and a cell permeability of the fusion protein may be remarkably high by comprising the histidine polymer thereby to visualize existence or expression level of the protease of live cells in real time (see Experiment example 1 and Experiment example 4).

Furthermore, due to self-assembly properties of the small heat shock protein in the fusion protein, the cage protein of the present invention may expose numerous recognition site of the protease on the outside the cage. Since, a ratio of the protease combined with the cage protein may increase by dozens to hundreds times, a strength of fluorescence per unit protein may greatly increase due to such high combining ratio. Particularly, the cage protein of the present invention may have fluorescence signal strength of about 20 to about 50 times higher than a single peptide of the conventional molecular imaging system (see Experiment example 3).

In addition, since the cage protein of the present invention based on protein may exhibit high biocompatibility by its nature, toxicity to cells or biological tissues may be very low compared with an imaging probe based on minerals or polymer (see Experiment example 5).

Meanwhile, a polynucleotide of the present invention may encode the fusion protein.

The polynucleotide of the present invention may be not limited to, preferably represented by the nucleotide sequence of SEQ ID NO: 4, which the nucleotide sequence of SEQ ID NO: 1 encoding a small heat shock protein derived from *Methanococcus jannaschii*, the nucleotide sequence of SEQ ID NO: 2 encoding a DEVD motif, and the nucleotide sequence of SEQ ID NO: 3 encoding a histidine polymer are sequentially linked (see Example 1-1).

In addition, an expression vector of the present invention may comprises the polynucleotide.

The expression vector of the present invention may not limited to, include a plasmid vector, a cosmid vector, a bacteriophage vector and a virus vector, etc. A suitable expression vector may be variously prepared by comprising not only expression regulatory sequence such as a promoter, an operator, an initiation codon, a terminal codon, a polyadenylation signal, and/or an enhancer but also a signal sequence for being targeted to the membranes or secretion, or a leader sequence, in accordance with the purpose. The promoter of the expression vector may be constitutive or inducible. Furthermore, the expression vector may comprises a selection marker to select host cells comprising the vector, and include a replication origin if the expression vector is capable of replication.

Figure 13:
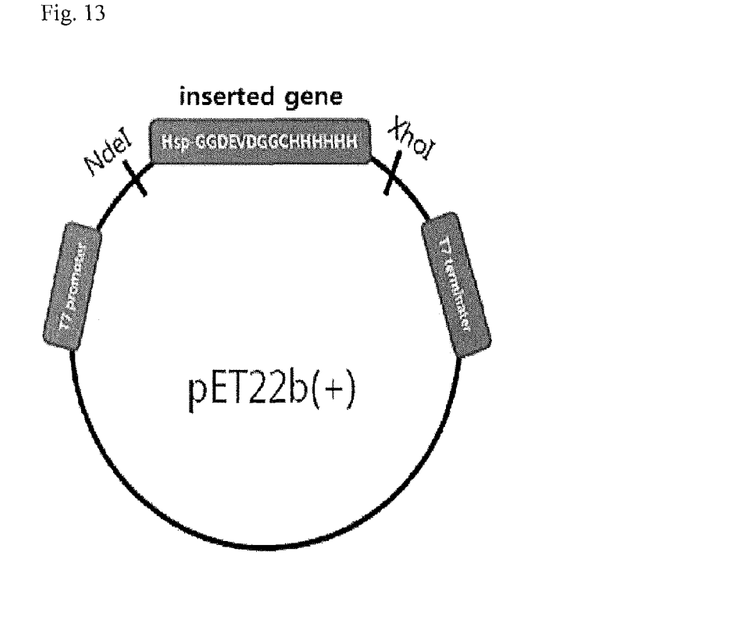
FIG. 13 is a cleavage map of an expression vector which the fusion protein of the present invention is inserted.

A recombinant expression vector of the present invention prepared as described above may be not limited to, preferably represented by a cleavage map of FIG. 13.

In addition, a transformant of the present invention may be transformed with the expression vector, preferably *E. coli*.

The transformation may include any method that introducing nucleic acids into a host cell, may be performed by transgenic techniques well known to those skilled. The transgenic techniques may be not limited to, preferably comprise microprojectile bombardment, electroporation, calcium phosphate ($CaPO_4$) transfection, calcium chloride (CaCl2) transfection, PEG-mediated fusion, microinjection and liposome-mediated method.

A biosensor for detecting protease of the present invention may comprise the cage protein of the present invention as an active ingredient.

The biosensor of the present invention may be useful to assay presence or expression level of the protease by including the cage protein of the present invention as an active ingredient. For example, when a DEVD (SEQ ID NO:8) motif is used as the recognition site of the protease in the fusion protein, presence or expression level of caspase may be detected by the biosensor. Furthermore, apoptosis in live cells may be visulized in real time (see Experiment example 4).

Thus, the biosensor of the present invention may be useful as a pharmaceutical composition for diagnosing. A target disease for diagnosing may be a disease caused by expression of the protease.

For instance, when the protease is caspase, the biosensor of the present invention may be used in the diagnosis of a disease selected from the group consisting of a cancer, an osteoarthritis, a rheumatoid arthritis, a dementia, an autoimmune disease and a stroke (MacFarlane, M.; Williams, A. C. EMBO reports 2004, 5(7), 674-678.). The cancer may be not limited to, preferably squamous cell carcinoma, uterine cancer, uterine cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, kidney cancer, bladder cancer, ovarian cancer, cholangiocarcinoma, gallbladder cancer, etc.

In addition, when the protease is MMP, the biosensor of the present invention may be used in the diagnosis of a disease selected from the group consisting of cancer invasion, arthritis and atherosclerosis (Van Lint, p.; Libert, C. J. Leukoc. Biol. 2007 82(6), 1375-1381.).

When the protease is Cathepsin S, the biosensor of the present invention may be used in the diagnosis of a disease selected from the group consisting of colorectal cancer, periodontitis, rheumatoid arthritis, atheriosclerosis, pancreatitis and gastritis (Kuester, D.; Lippert, H.; Roessner, A.; Krueger, S. Pathol. Res. Pract. 2008, 204(7), 491-500.).

When the protease is viral protease, the biosensor of the present invention may be used in the diagnosis of AIDS or a virus infection disease (Brik, A.; Wong, C. H. Org. Biomol. Chem. 2003 1(1), 5-14.).

A pharmaceutical composition of the present invention may include the biosensor of about 0.0001 to about 50 weight percent as an active ingredient based on a total weight of the composition. In addition to the active ingredient, the pharmaceutical composition of the present invention may comprise at least one active ingredient that represents the same or similar function to the active ingredient.

The pharmaceutical composition of the present invention may be prepared by comprising more than a kind of a pharmaceutically acceptable carrier in addition to the active ingredient above mentioned. The pharmaceutically acceptable carrier may be saline solution, sterilized water, ringer solution, buffered saline, dextrose solution, malto dextrin solution, glycerol, ethanol, a component of liposomes, and mixture thereof. Conventional additives such as antioxidants, buffers and fungistats may be added as needed. Additionally, by adding diluents, dispersants, surfactants, binders and lubricants, an injectable formulation such as an aqueous solution, a suspension, an emulsion, pills, capsules, granules or tablets formulations may be formed. The pharmaceutical composition of the present invention may be used by combining specific antibodies or other ligands with the carriers in order to act specifically on target organs. Furthermore, the pharmaceutical composition of the present invention may be prepared in an appropriate manner known in the art, or in a method described in Remington (Remington's Pharmaceutical Science (the latest edition), Mack Publishing Company, Easton Pa.) in accordance with diseases or ingredients. The pharmaceutical composition may be delivered in vivo via intravein, intraperitoneal, intramuscular, subcutaneous, intradermal, nasal, mucosal, inhalation and oral route, etc. Dose may vary depending on weight, age, gender, health status, diet, administration time, administration method, excretion and severity of disease of a target. A daily dose may be about 0.1 to about 100 mg/kg, preferably about 0.5 to about 10 mg/kg, it is more preferable that is administered once or divided into several times a day.

A bioactive material carrier of the present invention may be characterized that the bioactive material is loaded inside of the cage protein of the present invention.

The bioactive material is a material to be loaded inside of the cage protein of the present invention and to show activity when administered in vivo. The bioactive material may be not limited to, preferably selected from the group consisting of anticancer agents, antibiotics, hormones, cardiovascular drugs, gastrointestinal drugs and nervous system drugs. The drugs may be not limited to, preferably selected from the group consisting of small molecule drugs, proteins, peptides, nucleic acid including RNA, DNA or a modified nucleic acid, PNA, synthetic drugs, vaccines, immune regulators and insoluble drugs.

Specifically, the bioactive material is related to the protease in the protein cage of the present invention and may be a drug for prevention or treatment of disease induced by the protease.

For instance, when the protease is caspase, the bioactive material may be not limited to, preferably a medicine for prevention or treatment of disease such as a cancer, osteoarthritis, rheumatoid arthritis, dementia, autoimmune disease and stroke. The cancer may be not limited to, preferably include squamous cell carcinoma, uterine cancer, uterine cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, bladder cancer, ovarian cancer, cholangiocarcinoma, gallbladder cancer, etc. More preferably, the bioactive material may be not limited to, preferably selected from the group consisting of docetaxel, cisplatin, camptothecin, paclitaxel, tamoxifen, anasterozole, Gleevec, 5-FU, floxuridine, leuprolide, flutamide, zoledronate, doxorubicin, vincristine, gemcitabine, streptozocin, carboplatin, topotecan, belotecan, irinotecan, vinorelbine, hydroxyurea, Valrubicin, retinoic acid, methotrexate, meclorethamine, chlorambucil, busulfan, doxifluridine, vinblastin, mitomycin, prednisone, testosterone, mitoxantron, aspirin, salicylates, ibuprofen, naproxen, fenoprofen, indomethacin, phenyltazone, cyclophosphamide, mechlorethamine, dexamethasone, prednisolone, celecoxib, valdecoxib, nimesulide, cortisone and corticosteroid.

In addition, when the protease is MMP, the bioactive material may be not limited to, preferably a medicine for prevention or treatment of a disease selected from the group consisting of cancer invasion, arthritis and atherosclerosis, more preferably, may be a medicine selected from the group consisting of doxycycline, minocycline, marimastat and cipemastat.

In addition, when the protease is Cathepsin S, the bioactive material may be not limited to, preferably a medicine for prevention or treatment of a disease selected from the group consisting of colorectal cancer, periodontitis, rheumatoid arthritis, atheriosclerosis, pancreatitis and gastritis, more preferably, may be Z-Phe-Gly-NHO-Bz-pMe.

In addition, when the protease is viral protease, the bioactive material may be not limited to, preferably a medicine for prevention or treatment of AIDS or a virus infection disease, more preferably, may be saquinavir.

A method that the bioactive material is loaded into the cage protein of the present invention may be not limited to, preferably a bond using maleimide functional group on the inside of the cage, a bond using iodoacetyl functional group, a bond using pyridyl disulfide functional group or a bond using charge-charge interaction.

Especially, the bioactive material carrier of the present invention includes the cage protein having very excellent cell permeability, thereby to effectively deliver the bioactive material into the cells.

Thus, the bioactive materials carrier of the present invention may be used as an effective ingredient of a pharmaceutical composition for prevention or treatment of diseases caused by the expression of the protease, and details about the pharmaceutical composition are as described earlier.

The fusion protein of the present invention and the cage protein formed by its self-assembly properties are not cytotoxic and emit a fluorescence signal of about 20 to about 50 times higher comparing to a single peptide for the conventional molecular imaging per unit protein. In addition, the fusion protein and the cage protein have very excellent cell permeability, thereby to be effectively used for a biosensor or a bioactive material carrier.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Hereinafter, the present invention will be explained in detail with reference to the following examples.

However, the following examples illustrate the present invention, it should be understood that the present invention is not limited by the following examples.

EXAMPLE 1

Preparing of a Fusion Protein that a DEVD Motif and a Histidine Polymer are Linked to Hsp

EXAMPLE 1-1

Preparing an Expression Vector

In order to prepare a fusion protein that a DEVD (SEQ ID NO:8) motif and a histidine polymer are sequentially linked to Hsp (small heat shock protein), a recombinant method was used. Particularly, a sequence expressing the fusion protein was inserted into pET22b(+) (Novagen, US) as an expression vector of *E. coli*, and NdeI and XhoI as restriction enzymes.

The sequence expressing the fusion protein is represented by SEQ ID NO: 4, which SEQ ID NO: 1 encoding Hsp (small heat shock protein) derived from *Methanococcus jannaschii*, SEQ ID NO: 2 encoding a DEVD motif and SEQ ID NO: 3 encoding a histidine polymer are sequentially linked to.

Figure 1:
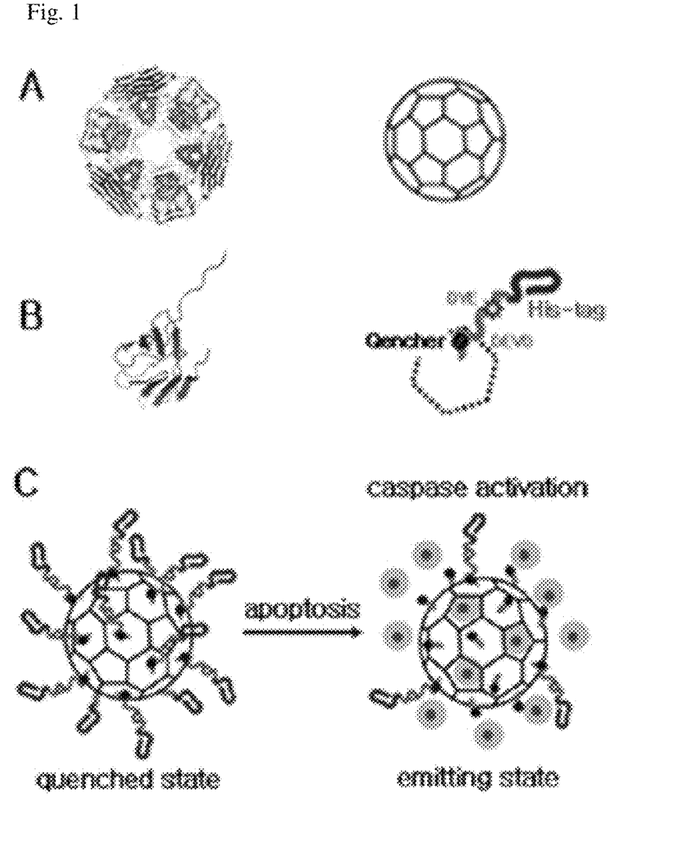
FIG. 1 is a schematic diagram of cage nanoparticles formed by self-assembly properties of a fusion protein in the present invention (A), a molecular model of a fusion protein as a unit (B), a schematic diagram of an apoptosis imaging (C).
Figure 2:
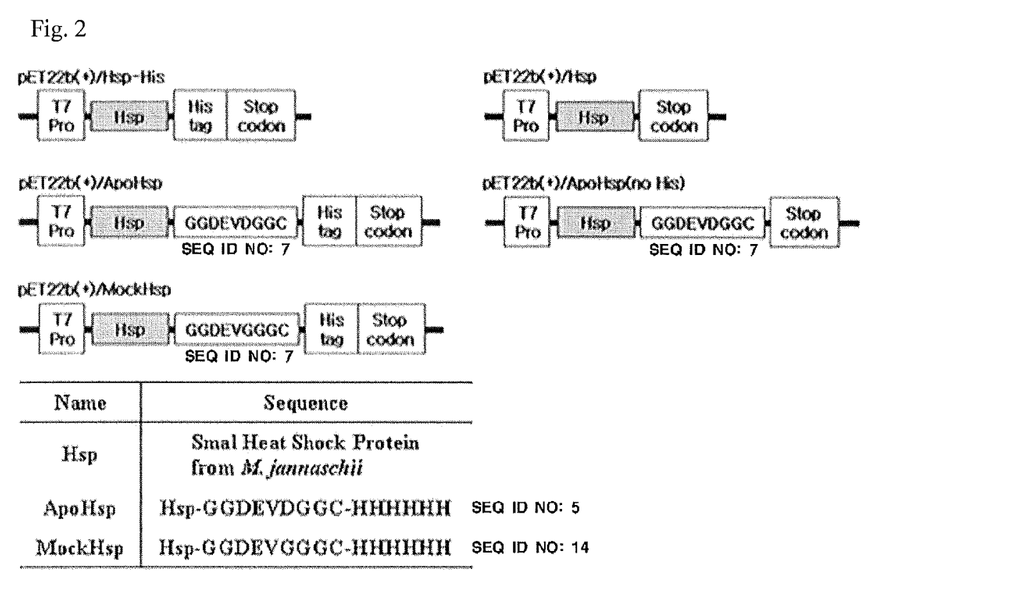
FIG. 2 is a schematic diagram showing that HSP, HSP-histidine tag, HSP-DEVD motif, HSP-DEVD motif-histidine tag and HSP-DEVG motif-histidine tag are inserted into an expression vector of pET22b(+), respectively.

As above, that sequence encoding Hsp, the DEVD (SEQ ID NO:8) motif and the histidine polymer were inserted to the expression vector of pET22b(+) (pET22b(+)/ApoHsp part) was schematized and shown in FIG. 2. A cleavage map of the expression vector that the fusion protein of the present invention was inserted was shown in FIG. 13.

EXAMPLE 1-2

Expression and Purification

*E. coli* was transformed in order to prepare the fusion protein using the expression vector prepared in the <Example 1-1>.

Particularly, BL21(DE3) host cell (New England Biolabs Inc) was transformed with the expression vector prepared in the <Example 1-1>, and then was cultivated in LB medium (Sigma-Aldrich Inc.) at 37° C. until OD600 value reaches 0.5. Expression was induced by adding IPTG (Isopropyl β-D thiogalactoside) of 1 mM.

Cells were collected after additional incubating for 6 hours and destroyed using lysis buffer (50 mM Tris-HCl, 8.0, 100 mM NaCl, 1 mM PMSF(phenylmethylsulfanylfluoride)). Soluble portions were used for purification.

For the purification, the fusion protein of the present invention was purified using an affinity chromatography and a size exclusion chromatography, and a molecular weight of purified protein was identified by SDS-PAGE (denaturing SDS-PAGE). The result was shown in FIG. 3.

Figure 3:
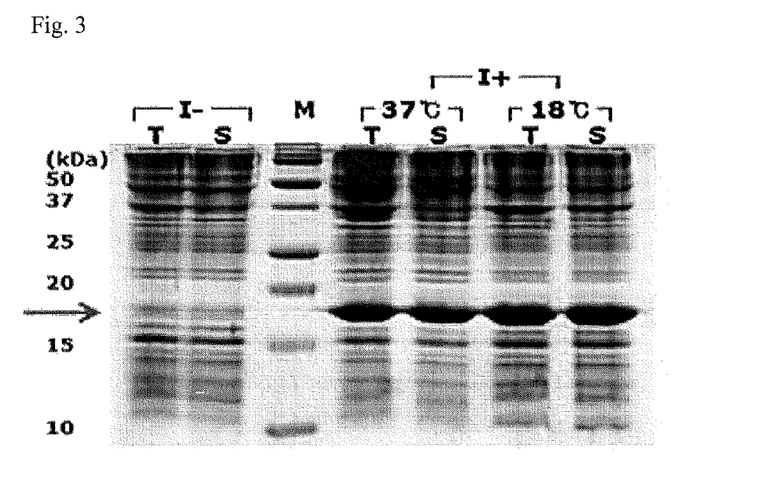
FIG. 3 shows results to identify an expression of the fusion protein by electrophoresis in *E. coli* transformed with the vector to which the fusion protein of the present invention is inserted (T: total fraction, S: soluble fraction, I—: IPTG, I+: no IPTG).

Particularly, Ni-NTA column (GE healthcare) was used in the affinity chromatography. After column preparation with A buffer (50 mM Tris-HCl, 8.0, 100 mM NaCl) and protein loading, and then washing, the proteins attached to the column were eluted with B buffer (50 mM Tris-HCl, 8.0, 100 mM NaCl, 500 mM Immidazole). And then the molecular weight of purified protein was identified by electrophoresis (Laemmli, U. K. Nature 1970, 227, 680-685.). In addition, Superdex 200 10/300 GL column (GE Healthcare) was used and injection volume was 2 mL and C buffer (PBS, pH 7.4) was used in the size exclusion chromatography As shown in FIG. 3, the fusion protein of the present invention was a size of 16.5 kDa and was identified to be represented by SEQ ID NO: 5 in sequencing result.

Figure 12:
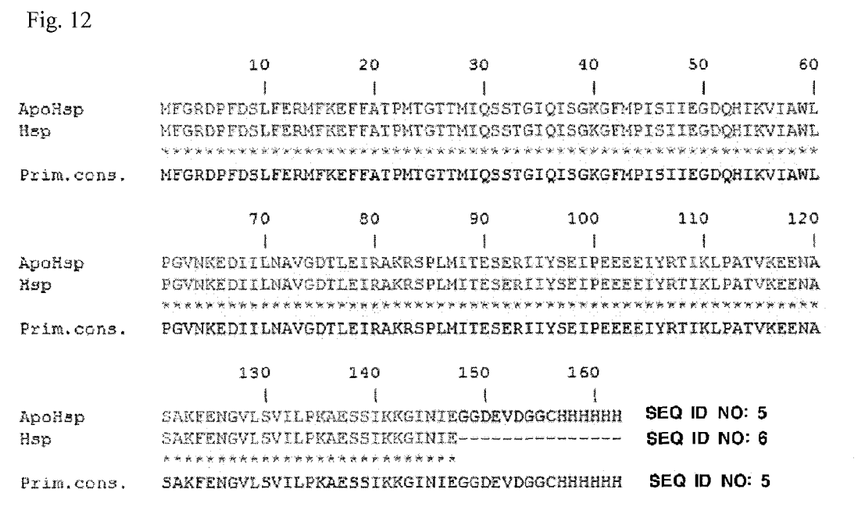
FIG. 12 show results comparing an amino acid sequence of the fusion protein of the present invention with an amino acid sequence of Hsp protein derived from *Methanococcus jannaschii*.

Furthermore, as shown in FIG. 12, it was identified that the DEVD (SEQ ID NO:8) motif and the histidine polymer were sequentially linked by comparing the an amino acid sequence of the fusion protein of the present invention with a sequence of Hsp protein derived from *Methanococcus jannaschii*.

EXAMPLE 1-3

Marker Insertion and Cage Formation

Figure 4:
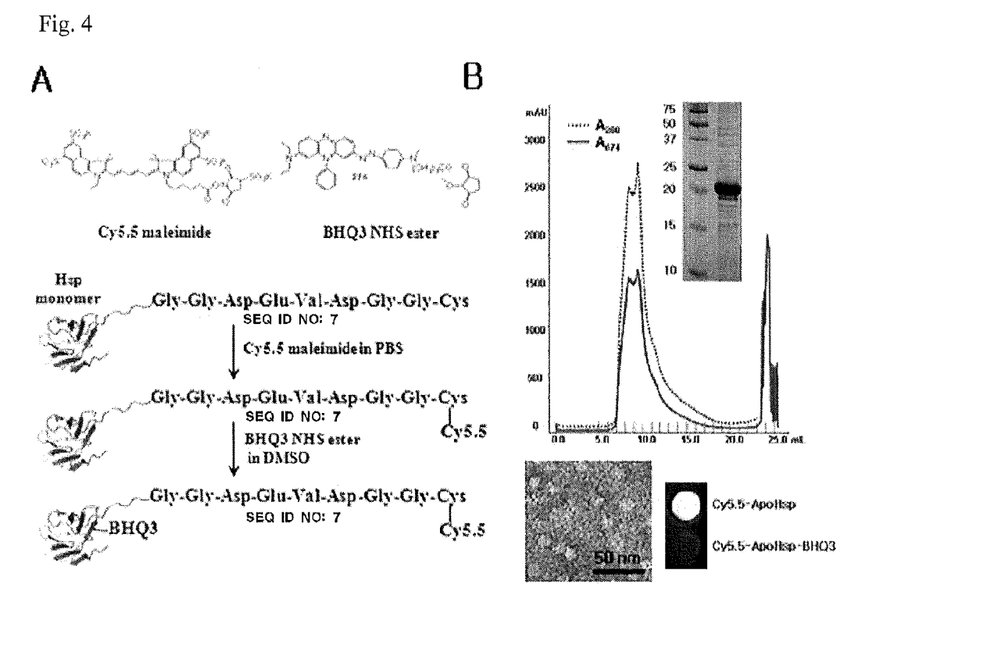
FIG. 4 is a schematic diagram showing that fluorescent substrate Cy5.5 and quencher BHQ3 are combined with the fusion protein of the present invention (A) and results showing that the fusion protein of the present invention combined with a marker forms a cage structure observed through a size exclusion chromatography, results showing the cage structure is formed observed through TEM assay, results showing that the cage protein combined with only fluorescent substrate, and the cage protein combined with the fluorescent substrate and the quencher observed through 12 bit CCD camera (KODAK, Japan) (B).

A fluorescence dye Cy5.5 (GE Healthcare) was inserted into the fusion protein prepared in the <Example 1-3>as a marker. Specifically, since the fusion protein was prepared including a cysteine residue in the DEVD (SEQ ID NO:8) motif, a fluorescence dye was selectively combined thereof. That is, the fluorescence dye Cy5.5 comprising maleimide to selectively form a covalent bond with a sulfhydryl group was formed a covalent bond with the cysteine residue of the fusion protein of the present invention (see FIG. 4A).

Particularly, Cy5.5 was melted in PBS buffer (pH 7.4), and then Cy5.5 was reacted with the fusion protein in the same buffer with excess. A molar ratio of the fusion protein to Cy 5.5 was 1:2. A reaction temperature was 4° C. and a reaction time was 4 hours (Fujiwara, K., et al. (1988). J. Immunol. Methods 112, 77-83).

After insertion of the marker, the fluorescence dye Cy5.5 was combined with a cage formed by the fusion protein of the present invention as a result of a size exclusion chromatography. Furthermore, it was identified that the combination did not interfere with a formation of the cage (see FIG. 4B).

Particularly, the size exclusion chromatography was performed with Superdex 200 10/300 GL column (GE Healthcare) and an injection volume of a sample was 2 mL. PBS buffer (pH 7.4) was used as a running buffer. Elution volume of the sample was equivalent to about 9 to about 10 mL, so that the fusion protein formed the cage was identified.

In addition, a cage shape was confirmed as a result of observation with transmission electron microscopy following negatively stained with uranyl acetate. A molecular weight of the fusion protein was about 19 kDa, that was verified with a marker on a SDS-PAGE. After the sample was collected in 96-well plate, it was verified that the fusion protein combined with Cy5.5 emitted fluorescence but the fluorescence was disappeared when BHQ3 quencher was attached (see FIG. 4B).

Additionally, it was verified that a fluorescence signal was quenched by combining a BHQ3 quencher (Black Hole Quencher, GE Healthcare) with the cage (see FIG. 4B). The BHQ3 quencher included NHS(N-Hydroxysuccinimide) ester group, to form a covalent bond using an amine group of 192 lysine residues (55th, 65th, 82th, 110th, 116th, 123th, 141th, 142th site of SEQ NO ID: 5×24 units) on a surface of the cage. Partially, the BHQ3 quencher was melted in PBS buffer (pH 7.4) and reacted with the fusion protein in the same buffer with excess at 4° C. for 4 hours. A molar ratio of the fusion protein to BHQ3 was 1:2 (Fujiwara, K., et al. (1988). J. Immunol. Methods 112, 77-83.).

Finally, as shown in FIG. 4, a quenching phenomenon between a fluorescent substance and a quencher was possible due to a unique symmetrical structure of the cage formed by the fusion protein of the present invention. Also, a close distance between the fluorescent substance and the quencher was contributed to the quenching phenomenon. As described above, the cage formed by the fusion protein of the present invention was named ApoHsp.

EXPERIMENT EXAMPLE 1

Cell Permeability of the Cage Formed by the Fusion Protein of the Present Invention A cell permeability test for CT26 (Ojo-Amaize, E. A. et al. World J. Gastroenterol. 2007, 13(34), 4586-4588.) as a mouse colon carcinoma cell line, HT29 (Lu, X. et al. Cancer Research 1992, (52), 3718-3725) as a human colon cancer cell line, MDA-MB231 (Cassoni, P. et al. Journal of Cancer 1998, 72(2), 340-344.) as a human breast cancer cell line, HeLa cell derived from a human cervical carcinoma (Qu, X. et al. J. Biochem. Mol. Biol. 2004, 37(4), 445-453.) was carried out in order to identify a cell permeability of the cage formed by the fusion protein of the present invention in the Example 1-3.

Figure 5:
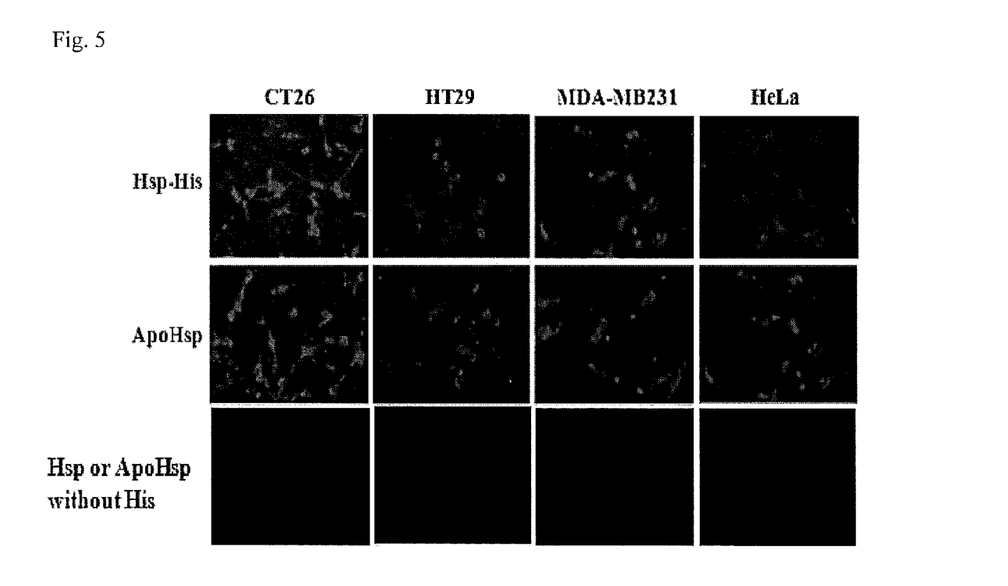
FIG. 5 is a picture showing a cell permeability of HSP or ApoHSP combined with a histidine polymer to various cells.

Particularly, ApoHsp fused with the histidine polymer and HSP were treated with about 10 ug/ml in the cells, and the results were analyzed and shown in FIG. 5.

More particularly, for each three kinds of Hsp-His and ApoHsp fused with the histidine polymer, and just HSP, Cy5.5 having maleimide was combined with a lysine site on the outside of the cage. After treating with about 10 ug/ml in the cells, the cells were observed with a microscope per hour. The microscope for observation was Axioskop2 FS plus imaging microscope (ZEISS) to which Achroplan IR40 x/0.80 W lens, a fluorescence filter (Omega optical) for Cy5.5, Axiocam black and which white CCD camera (Carl Zeiss) are attached.

As shown in FIG. 5, ApoHsp and HSP fused with the histidine polymer all showed excellent cell permeability in one hour, but HSP not fused with the histidine polymer was not able to permeable within the cell.

As above with the results, the histidine polymer introduced to the fusion protein of the present invention was manifoldly exposed to the outside of a self-assembled cage, thereby the cage is estimated to have the cell permeability.

EXPERIMENT EXAMPLE 2

Substrate Specificity of the Case Formed by the Fusion Protein of the Present Invention In order to identify whether the cage formed by the fusion protein of the present invention in the Example 1-3 responds to a specific caspase, response to various caspases such as caspase-3 (NCBI accession no: NP_004337.2), caspase-7 (NCBI accession no: NP_001218.1.), caspase-8(NCBI accession no: NP_001073593.1) and caspase-9 (NCBI accession no: NP_001220.2.) derived from human was identified. The results were shown in FIGS. 6 and 7.

Particularly, the cage protein of 10 ug was reacted with caspase-3, caspase-7, caspase-8 and caspase-9 (purchased from R&D Systems) respectively using a 96-well plate at 37° C. for 2 hours. Fluorescence was observed with 12 bit CCD camera (Kodak, Japan) on which Special C mount lens and Cy5.5 bandpass emission filter (680 to 720 nm, Omega Optical) ware mounted. A composition of a reaction buffer was 25 mM HEPES, pH 7.5, 0.1% CHAPS, and 10 mM DTT. A control reaction without enzyme did not cause fluorescence at all.

Figure 6:
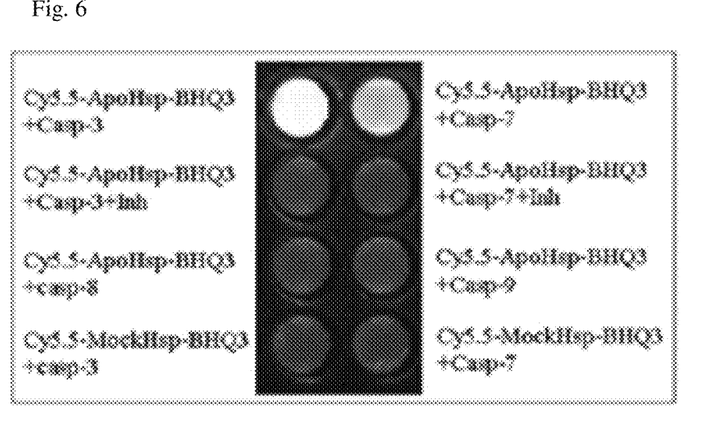
FIG. 6 is a picture showing that the cage protein of the present invention is specific for caspase-3 and caspase-7 since the cage protein of the present invention specifically responds to caspase-3 and caspase-7 and does not emit fluorescence for other capases, particularly since fluorescence does not occur at all when caspase-3 inhibitor is added.
Figure 7:
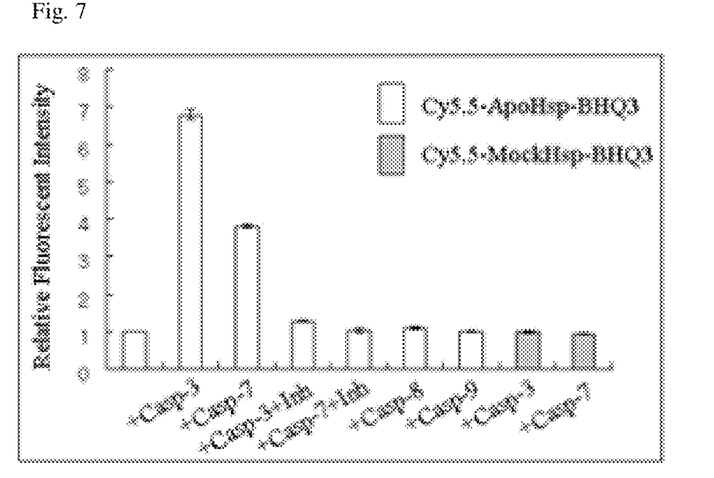
FIG. 7 is a graph comparing fluorescence of the reactants in FIG. 6 measured by fluorescence spectroscopy, respectively.

As shown FIGS. 6 and 7, ApoHsp in a reaction with caspase-3 showed about 7 times greater fluorescence signal compared to an extinction condition, and ApoHsp in a reaction with caspase-7 showed about 4 times greater fluorescence signal. However, fluorescence did not occur in reactions with another two capases at all. Thus, it was verified that the cage protein was most specifically reacted with capase-3. In addition, since fluorescence of ApoHsp significantly decreased when treated with Z-DEVD-FMK (SEQ ID NO:13) (R&D Systems) as a caspase-3 inhibitor, the cage protein was known to be specifically combined with capase-3, too.

EXPERIMENT EXAMPLE 3

Fluorescence Resilience of the Cage Formed by the Fusion Protein of the Present Invention In order to identify fluorescence resilience of ApoHsp which is the cage formed by the fusion protein of the present invention, that is, in order to identify whether ApoHsp combines with a substrate with high efficiency, a probe based on a single-peptide used for a conventional molecular imaging was prepared and compared.

Particularly, Cy5.5 and BHQ3 were respectively combined with a cysteine residue and an amino group of N-terminal in a polypeptide of SEQ ID NO: 7 including a DEVD (SEQ ID NO:8) motif. Then, fluorescence occurred by reacting with caspase-3 was compared with ApoHsp and the results were shown in FIG. 8.

Figure 8:
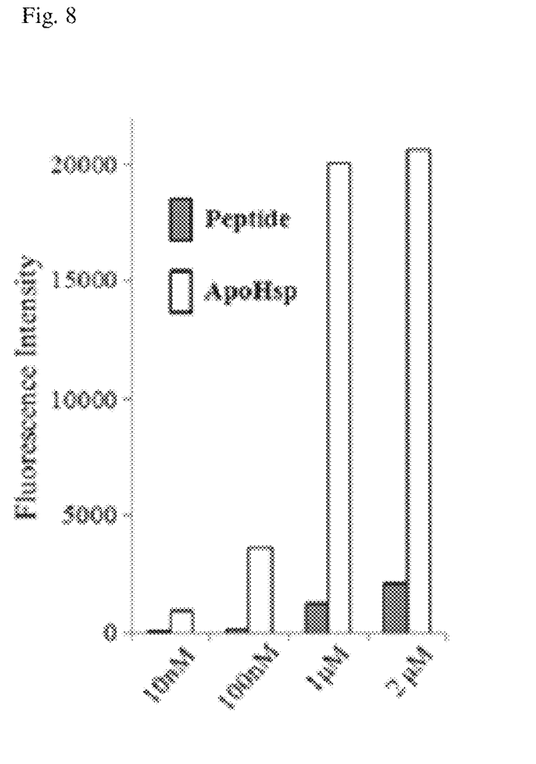
FIG. 8 is a graph comparing fluorescence of the cage protein of the present invention with a probe of a single peptide in the same concentration.

As shown in FIG. 8, a fluorescence signal of ApoHsp increased by 20 to 50 times higher than the single peptide. Through the results, it was verified that the cage formed by the fusion protein of the present invention combined with the substrate with high efficiency compared to the single peptide used for the conventional molecular imaging

EXPERIMENT EXAMPLE 4

Figure 10:
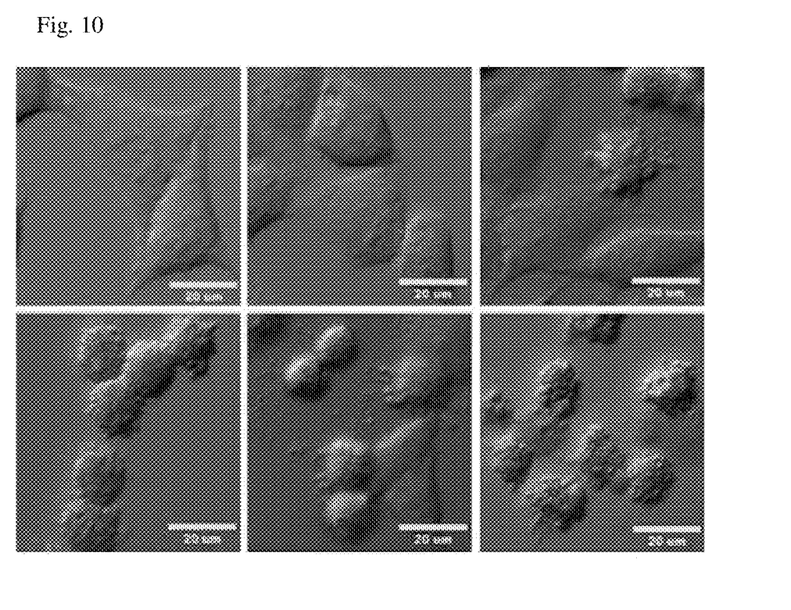
FIG. 10 is a picture showing real-time imaging of apoptosis using the cage protein of the present invention (from the upper left to the right: normal cells, 10 minutes after apoptosis, 30 minutes after apoptosis, from the bottom left to the right: 1 hour after apoptosis, 2 hours after apoptosis, MockHsp treatment instead of ApoHsp).

Real-time Imaging of Apoptosis of the Cage Formed by the Fusion Protein of the Present Invention Apoptosis in a live cell using ApoHsp of the present invention was visualized and the results were shown in FIG. 10.

Particularly, HeLa cell (1×105) grown in coverslip was reacted with ApoHsp in PBS buffer including CaCl2 and MgCl2 of 100 µg/mL at 37° C. for 1 hour and then was stabilized in DMEM (dulbecco's modified eagle's medium) for 1 hour. Apoptosis was induced by treating with TNF-related apoptosis-inducing ligand (TRAIL) of 50 ng/mL and it was observed using fluorescence microscope IX81-ZDC (OLYMPUS) to which 12 bit CCD camera CoolSNAP fx (Photometrics) was attached. Imaging analysis was performed by MetaMorph (Molecular Devices).

As shown in FIG. 10, when apoptosis was induced by treating cell treated ApoHsp with TRAIL (R&D Systems), fluorescence was observed after approximately 10 minutes and maximum fluorescence was observed within 1 hour. However, in case MockHsp unaware of caspase by a modification of a DEVD (SEQ ID NO:8) motif, fluorescence was not observed at all.

Figure 11:
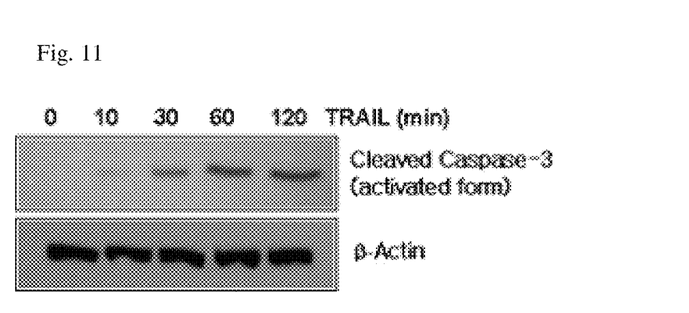
FIG. 11 shows results of western blotting using an antibody in order to detect activity and expression level of caspase-3 to be activated by an apoptosis inducer in the cell.

Furthermore, in order to identify whether capase-3 is activated in apoptosis using TRAIL, western blotting was carried out using antibody to recognize only activated caspase-3 (anti-caspase-3 antibody, Cell Signaling Technology Inc.). It was confirmed that activated caspase-3 increased in accordance with hours after TRAIL treatment (see FIG. 11).

Particularly, after treating HeLa cell with TRAIL, the cells were destroyed with lysis buffer (1% SDS, 10% glycerol, 10% 2-mercaptoethanol, 0.001% Bromophenol Blue, 50 mM Tris/HCl, pH 6.8). A sample of about 10 ug was loaded in 18% SDS polyacrylamide gel and electrophoresis was carried out, and then transferred to a nitrocellulose membrane. A detailed process was referred to a citation (Scaffidi, C.; Fulda, S.; Srinivasan, A. EMBO J. 1998, 17, 1675-1687.).

EXPERIMENT EXAMPLE 5

Figure 9:
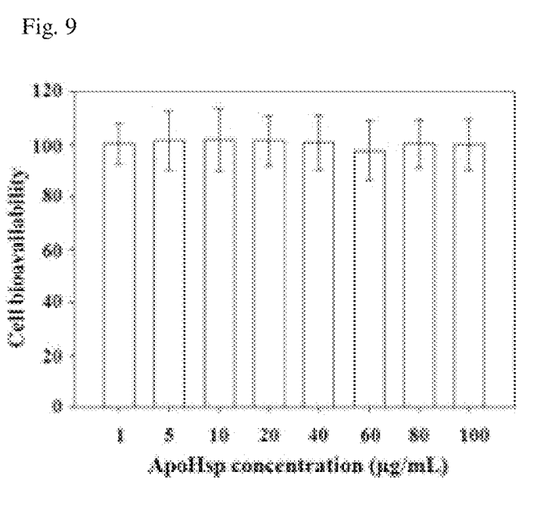
FIG. 9 is a graph showing the results of MMT assay performed in order to verify biocompatibility of the cage protein of the present invention.

Biocompatibility of the Cage Protein Formed by the Fusion Protein of the Present Invention In order to evaluate a biocompatibility of the cage protein and ApoHsp formed by the fusion protein of the present invention, MTT assay was carried out and the results were shown in FIG. 9.

Particularly, after HeLa cell in exponential growth phase was grown in 96-well plate until 20000 cells/well, ApoHsp was treated with concentrations of 1 to 100 ug/mL in each well and cultivated for 24 hours. MTT solution of 0.5 mg/mL was added to each well with 200 uL and reacted for 4 hours. After reaction with DMSO of 200 uL for 10 minutes, absorbance was measured using ELISA at a wavelength of 570 nm. More detailed process was referred to a citation (Choi, Y. H.; Liu, F.; Kim, J S; Choi, Y. K.; Park, J. S.; Kim, S. W. J. Control. Rel. 1998, 54, 39-48.).

As shown in FIG. 9, although a concentration of ApoHsp increased to 100 ug/ml, numbers of cell did not decrease compared to that not treated with ApoHsp at all. This is shown that ApoHsp of the present invention is very biocompatible and not toxic. However, it has been reported that an apoptosis probe based on a polymer (Kim, K. M. et al. 2006) shows cytotoxicity at a concentration of more than 20 ug/ml and about 50% of cells only survive at a concentration of about 100 ug/ml.

What is claimed is:

1. A fusion protein for detecting a protease, wherein the fusion protein comprises:
   a small heat shock protein (Hsp) consisting of the amino acid sequence of SEQ ID NO:6,
   a protease recognition site consisting of the amino acid sequence of SEQ ID NO: 7, and
   a histidine polymer,
   wherein the recognition site and the histidine polymer are sequentially linked to the carboxyl terminal of the small heat shock protein and wherein the cysteine of the protease recognition site is labeled with a fluorescent substance, and an amino acid of the small heat shock protein is labeled with a quencher of the fluorescent substance.

2. The fusion protein of claim 1, wherein the protease is a caspase.

3. The fusion protein of claim 1, wherein the histidine polymer comprises 6 to 20 histidine residues that are consecutively linked.

4. The fusion protein of claim 3, wherein the histidine polymer consists of the amino acid sequence of SEQ ID NO: 9.

5. The fusion protein of claim 1, wherein the fusion protein consists of the amino acid sequence of SEQ ID NO: 5.

6. A cage protein comprising the fusion protein of to claim 1.

7. The cage protein of claim 6, wherein the cage protein is formed from the fusion proteins as regularly arranged unit.

8. A biosensor for detecting a protease, wherein the biosensor comprises the cage protein of claim 6.

9. The biosensor of claim 8, wherein the protease is a caspase.

* * * * *

SEQUENCE LISTING

```
<160> NUMBER OF SEQ ID NOS: 12

<210> SEQ ID NO 1
<211> LENGTH: 441
<212> TYPE: DNA
<213> ORGANISM: Artificial Sequence
<220> FEATURE:
<223> OTHER INFORMATION: polynucleotide for encoding Hsp

<400> SEQUENCE: 1
atgttcggaa gagacccatt tgattcatta tttgaaagaa tgtttaaaga gtttttttgca      60 acaccaatga caggaaccac aatgattcaa agctcaacag gaatacaaat ttctggaaaa     120
gggttcatgc caatctcaat tattgaagga gaccagcata taaaagttat tgcatggttg     180
ccaggggtta ataaagagga cataattta aatgcagttg gagatacatt agagattaga     240
gctaagagaa gcccattaat gataactgag agtgaaagaa ttatctactc agaaattcca     300
gaagaggaag aaatatatag aacaataaaa cttcctgcaa ctgttaagga agaaaatgcc     360
tcagctaagt tgaaaatgg tgttttatca gttatattac caaaggcaga atcctcaatt     420
aagaaaggaa tcaacattga a                                              441
```

<210> SEQ ID NO 2
<211> LENGTH: 27
<212> TYPE: DNA
<213> ORGANISM: Artificial Sequence
<220> FEATURE:
<223> OTHER INFORMATION: polynucleotide for encoding DEVD motif

<400> SEQUENCE: 2
ggcggcgatg aagtggatgg cggctgc                                    27

<210> SEQ ID NO 3
<211> LENGTH: 18
<212> TYPE: DNA
<213> ORGANISM: Artificial Sequence
<220> FEATURE:
<223> OTHER INFORMATION: polynucleotide for encoding hexahistidine-tag

<400> SEQUENCE: 3
catcatcatc atcatcat                                              18

<210> SEQ ID NO 4
<211> LENGTH: 486
<212> TYPE: DNA
<213> ORGANISM: Artificial Sequence
<220> FEATURE:
<223> OTHER INFORMATION: polynucleotide encoding for fusion protein
      (HSP-DEVD motif-hexahistidine)

<400> SEQUENCE: 4
atgttcggaa gagacccatt tgattcatta tttgaaagaa tgtttaaaga gttttttgca    60
acaccaatga caggaaccac aatgattcaa agctcaacag gaatacaaat ttctggaaaa   120
gggttcatgc caatctcaat tattgaagga gaccagcata taaaagttat tgcatggttg   180
ccaggggtta ataaagagga cataatttta aatgcagttg gagatacatt agagattaga   240
gctaagagaa gcccattaat gataactgag agtgaaagaa ttatctactc agaaattcca   300
gaagaggaag aaatatatag aacaataaaa cttcctgcaa ctgttaagga gaaaaatgcc   360
tcagctaagt ttgaaaatgg tgttttatca gttatattac caaaggcaga atcctcaatt   420
aagaaaggaa tcaacattga aggcggcgat gaagtggatg gcggctgcca tcatcatcat   480
catcat                                                             486

<210> SEQ ID NO 5
<211> LENGTH: 162
<212> TYPE: PRT
<213> ORGANISM: Artificial Sequence
<220> FEATURE:
<223> OTHER INFORMATION: polypeptide for fusion protein (HSP-DEVD
      motif-hexahistidine)

<400> SEQUENCE: 5

Met Phe Gly Arg Asp Pro Phe Asp Ser Leu Phe Glu Arg Met Phe Lys
 1               5                  10                  15

Glu Phe Phe Ala Thr Pro Met Thr Gly Thr Thr Met Ile Gln Ser Ser
            20                  25                  30

Thr Gly Ile Gln Ile Ser Gly Lys Gly Phe Met Pro Ile Ser Ile Ile
        35                  40                  45

Glu Gly Asp Gln His Ile Lys Val Ile Ala Trp Leu Pro Gly Val Asn
    50                  55                  60

Lys Glu Asp Ile Ile Leu Asn Ala Val Gly Asp Thr Leu Glu Ile Arg
65                  70                  75                  80

-continued

```
Ala Lys Arg Ser Pro Leu Met Ile Thr Glu Ser Glu Arg Ile Ile Tyr
            85                  90                  95

Ser Glu Ile Pro Glu Glu Glu Glu Ile Tyr Arg Thr Ile Lys Leu Pro
        100                 105                 110

Ala Thr Val Lys Glu Glu Asn Ala Ser Ala Lys Phe Glu Asn Gly Val
    115                 120                 125

Leu Ser Val Ile Leu Pro Lys Ala Glu Ser Ser Ile Lys Lys Gly Ile
130                 135                 140

Asn Ile Glu Gly Gly Asp Glu Val Asp Gly Gly Cys His His His His
145                 150                 155                 160

His His

<210> SEQ ID NO 6
<211> LENGTH: 147
<212> TYPE: PRT
<213> ORGANISM: Artificial Sequence
<220> FEATURE:
<223> OTHER INFORMATION: polypeptide for HSP

<400> SEQUENCE: 6

Met Phe Gly Arg Asp Pro Phe Asp Ser Leu Phe Glu Arg Met Phe Lys
1               5                   10                  15

Glu Phe Phe Ala Thr Pro Met Thr Gly Thr Thr Met Ile Gln Ser Ser
            20                  25                  30

Thr Gly Ile Gln Ile Ser Gly Lys Gly Phe Met Pro Ile Ser Ile Ile
        35                  40                  45

Glu Gly Asp Gln His Ile Lys Val Ile Ala Trp Leu Pro Gly Val Asn
    50                  55                  60

Lys Glu Asp Ile Ile Leu Asn Ala Val Gly Asp Thr Leu Glu Ile Arg
65                  70                  75                  80

Ala Lys Arg Ser Pro Leu Met Ile Thr Glu Ser Glu Arg Ile Ile Tyr
            85                  90                  95

Ser Glu Ile Pro Glu Glu Glu Glu Ile Tyr Arg Thr Ile Lys Leu Pro
        100                 105                 110

Ala Thr Val Lys Glu Glu Asn Ala Ser Ala Lys Phe Glu Asn Gly Val
    115                 120                 125

Leu Ser Val Ile Leu Pro Lys Ala Glu Ser Ser Ile Lys Lys Gly Ile
130                 135                 140

Asn Ile Glu
145

<210> SEQ ID NO 7
<211> LENGTH: 9
<212> TYPE: PRT
<213> ORGANISM: Artificial Sequence
<220> FEATURE:
<223> OTHER INFORMATION: polypeptide for DEVD motif

<400> SEQUENCE: 7

Gly Gly Asp Glu Val Asp Gly Gly Cys
1               5

<210> SEQ ID NO 8
<211> LENGTH: 4
<212> TYPE: PRT
<213> ORGANISM: Artificial Sequence
<220> FEATURE:
<223> OTHER INFORMATION: unit sequence for DEVD motif

<400> SEQUENCE: 8
```

```
Asp Glu Val Asp
  1

<210> SEQ ID NO 9
<211> LENGTH: 6
<212> TYPE: PRT
<213> ORGANISM: Artificial Sequence
<220> FEATURE:
<223> OTHER INFORMATION: polypeptide for histitine polymer

<400> SEQUENCE: 9

His His His His His His
  1               5

<210> SEQ ID NO 10
<211> LENGTH: 7
<212> TYPE: PRT
<213> ORGANISM: Artificial Sequence
<220> FEATURE:
<223> OTHER INFORMATION: recognition site of MMP

<400> SEQUENCE: 10

Ile Pro Val Ser Leu Arg Ser
  1               5

<210> SEQ ID NO 11
<211> LENGTH: 4
<212> TYPE: PRT
<213> ORGANISM: Artificial Sequence
<220> FEATURE:
<223> OTHER INFORMATION: recognition site of cathepsin S
<220> FEATURE:
<222> LOCATION: 4
<223> OTHER INFORMATION: represents any kind of amino acid

<400> SEQUENCE: 11

Val Val Arg Xaa
  1

<210> SEQ ID NO 12
<211> LENGTH: 10
<212> TYPE: PRT
<213> ORGANISM: Artificial Sequence
<220> FEATURE:
<223> OTHER INFORMATION: recognition site of viral proteases

<400> SEQUENCE: 12

Val Ser Gln Asn Tyr Pro Ile Val Gln Asn
  1               5                  10
```